US010786157B2

(12) United States Patent
Dalene

(10) Patent No.: US 10,786,157 B2
(45) Date of Patent: Sep. 29, 2020

(54) SPECTROPHOTOMETRIC SENSOR

(71) Applicant: Edwards Lifesciences Corporation, Irvine, CA (US)

(72) Inventor: Matthew Dalene, Clinton, CT (US)

(73) Assignee: Edwards Lifesciences Corporation, Irvine, CA (US)

(*) Notice: Subject to any disclaimer, the term of this patent is extended or adjusted under 35 U.S.C. 154(b) by 764 days.

(21) Appl. No.: 14/947,809

(22) Filed: Nov. 20, 2015

(65) Prior Publication Data

US 2016/0143537 A1 May 26, 2016

Related U.S. Application Data

(60) Provisional application No. 62/082,437, filed on Nov. 20, 2014.

(51) Int. Cl.
*A61B 5/00* (2006.01)
*A61B 5/1455* (2006.01)

(52) U.S. Cl.
CPC ........ *A61B 5/0075* (2013.01); *A61B 5/14552* (2013.01); *A61B 5/6833* (2013.01); *A61B 2560/0412* (2013.01); *A61B 2562/0238* (2013.01); *A61B 2562/164* (2013.01); *G01N 2201/0621* (2013.01)

(58) Field of Classification Search
CPC .................................................. A61B 5/0075
See application file for complete search history.

(56) References Cited

U.S. PATENT DOCUMENTS

| | | |
|---|---|---|
| 2002/0016536 A1 | 2/2002 | Benni |
| 2004/0024297 A1 | 2/2004 | Chen et al. |
| 2006/0189861 A1 | 8/2006 | Chen et al. |
| 2006/0195024 A1 | 8/2006 | Benni |
| 2008/0017800 A1 | 1/2008 | Benni |
| 2009/0182209 A1 | 7/2009 | Benni |
| 2009/0281403 A1 | 11/2009 | Benni |
| 2010/0105998 A1 | 4/2010 | Benni |
| 2011/0028812 A1 | 2/2011 | Benni |
| 2011/0118574 A1 | 5/2011 | Chang et al. |
| 2011/0237910 A1 | 9/2011 | Gamelin et al. |
| 2012/1096610 * | 2/2012 | Duffy .................. A61B 5/1455 600/323 |
| 2012/0065485 A1 | 3/2012 | Benni et al. |
| 2012/0108927 A1 | 5/2012 | Chen et al. |
| 2012/0179011 A1 | 7/2012 | Moon et al. |
| 2013/0012822 A1 | 1/2013 | Kosturko et al. |

(Continued)

OTHER PUBLICATIONS

EP search report for EP15275238.2 dated Mar. 23, 2016.

*Primary Examiner* — Rochelle D Turchen
(74) *Attorney, Agent, or Firm* — Getz Balich LLC

(57) ABSTRACT

A near-infrared spectroscopy (NIRS) sensor assembly for measuring a characteristic of a biological tissue is provided. The NIRS sensor assembly includes a light source, at least one light detector, and a layer disposed within the sensor assembly. The light source is operable to emit light at one or more predetermined wavelengths. The at least one light detector has an active area for detecting light emitted by the light source and passed through the biological tissue. The light detector is operable to produce signals representative of the detected light. The layer disposed within the sensor assembly has at least one deflection element.

13 Claims, 11 Drawing Sheets

(56) References Cited

U.S. PATENT DOCUMENTS

| | | |
|---|---|---|
| 2013/0023744 A1 | 1/2013 | Benni |
| 2013/0204105 A1 | 8/2013 | Benni |
| 2014/0051956 A1 | 2/2014 | Dalene et al. |
| 2014/0094668 A1 | 4/2014 | Benni |
| 2014/0100823 A1 | 4/2014 | Kosturko |
| 2014/0121481 A1 | 5/2014 | Abrams et al. |
| 2014/0171761 A1 | 6/2014 | Dalene et al. |
| 2014/0206976 A1 | 7/2014 | Thompson et al. |
| 2015/0087948 A1* | 3/2015 | Bishay .................. A61B 5/6801 600/382 |
| 2015/0099950 A1* | 4/2015 | Al-Ali .................. A61B 5/7275 600/323 |
| 2015/0308946 A1 | 10/2015 | Duffy et al. |
| 2016/0256665 A1* | 9/2016 | Doshi .................. A61F 13/0226 |
| 2017/0296317 A1* | 10/2017 | Gordon ............... A61M 5/1452 |

\* cited by examiner

SPECTROPHOTOMETRIC SENSOR

This application claims priority to U.S. Patent Appln. No. 62/082,437 filed Nov. 20, 2014, which is hereby incorporated by reference.

BACKGROUND OF THE INVENTION

1. Technical Field

Aspects of the present invention generally relate to non-invasive spectrophotometric medical devices, and more particularly relate to non-invasive medical devices that include a sensor with a subject contact layer.

2. Background Information

Non-invasive medical devices (e.g., near-infrared spectroscopy (NIRS) sensor assemblies, pulse oximetry sensor assemblies, etc.) often include one or more light emitting components (e.g., light emitting diodes (LEDs), laser diodes, etc.) that emit light signals (e.g., visible light signals, near-infrared light signals, etc.) and one or more light detecting components (e.g., photodiodes, charge-coupled devices, etc.) that detect light signals emitted by the light emitting components, for example, after such light signals pass through a biological tissue.

SUMMARY OF THE INVENTION

According to an aspect of the present disclosure, a near-infrared spectroscopy (NIRS) sensor assembly for measuring a characteristic of a biological tissue is provided. The NIRS sensor assembly includes a light source, at least one light detector, and a layer disposed within the sensor assembly. The light source is operable to emit light at one or more predetermined wavelengths. The at least one light detector has an active area for detecting light emitted by the light source and passed through the biological tissue. The light detector is operable to produce signals representative of the detected light. The layer disposed within the sensor assembly has at least one deflection element.

In one or more embodiments of the above described aspect, the layer disposed within the sensor assembly is a pad having a top surface, a bottom surface, and at least one side surface extending between the top and bottom surfaces.

In one or more embodiments of the above described aspect and embodiments, the at least one deflection element is disposed in at least one of the top or bottom surfaces.

In one or more embodiments of the above described aspect and embodiments, the at least one deflection element does not break through a side surface.

In one or more embodiments of the above described aspect and embodiments, the at least one deflection element extends between the bottom surface and the top surface, thereby providing an open passage between the bottom surface and the top surface.

In one or more embodiments of the above described aspect and embodiments, the deflection element is configured as a slot.

In one or more embodiments of the above described aspect and embodiments, the at least one deflection element includes a plurality of voids aligned with one another, extending between the bottom surface and the top surface.

In one or more embodiments of the above described aspect and embodiments, the at least one deflection element has a width and a depth, which depth distance extends from an opening in one of the bottom surface or the top surface and extends toward the other of the top surface or bottom surface, and which depth distance is less than the distance between the top surface and the bottom surface.

In one or more embodiments of the above described aspect and embodiments, the depth is uniform along the length of the deflection element.

In one or more embodiments of the above described aspect and embodiments, the deflection element is configured as a channel.

In one or more embodiments of the above described aspect and embodiments, the sensor assembly includes a plurality of the deflection elements aligned with one another.

In one or more embodiments of the above described aspect and embodiments, the at least one deflection element includes at least one first deflection element having an opening disposed in the bottom surface, at least one second deflection element having an opening disposed in the top surface.

In one or more embodiments of the above described aspect and embodiments, the at least one first deflection element is offset from the at least one second deflection element.

In one or more embodiments of the above described aspect and embodiments, the at least one first deflection element is aligned with the at least one second deflection element.

In one or more embodiments of the above described aspect and embodiments, the deflection element has a length and a uniform width along the length of the deflection element.

In one or more embodiments of the above described aspect and embodiments, the at least one deflection element includes a deflection element that extends between the bottom surface and the top surface, thereby providing an open passage between the bottom surface and the top surface.

In one or more embodiments of the above described aspect and embodiments, the sensor assembly includes a plurality of deflection elements, and the deflection elements are positioned relative to the pad for specific application type having a predetermined surface curvature.

In one or more embodiments of the above described aspect and embodiments, the at least one light detector includes a near light detector spaced a first distance from the light source and a far light detector spaced a second distance from the light source, which second distance is greater than the first distance, and the at least one deflection element includes a first deflection element disposed between the near light detector and the far light detector, a second deflection element disposed between the near light detector and the light source, a third deflection element disposed on a first lateral side of the light source, and a fourth deflection element disposed on a second lateral side of the light source, opposite the first lateral side.

The above described aspects of the present invention and embodiments may be used individually or in combination with one another, and the present invention is not limited to any particular configuration. These and other aspects, embodiments, features, and advantages of the present invention will become apparent in light of the detailed description of the invention provided below, and as illustrated in the accompanying drawings.

DETAILED DESCRIPTION

Figure 1:
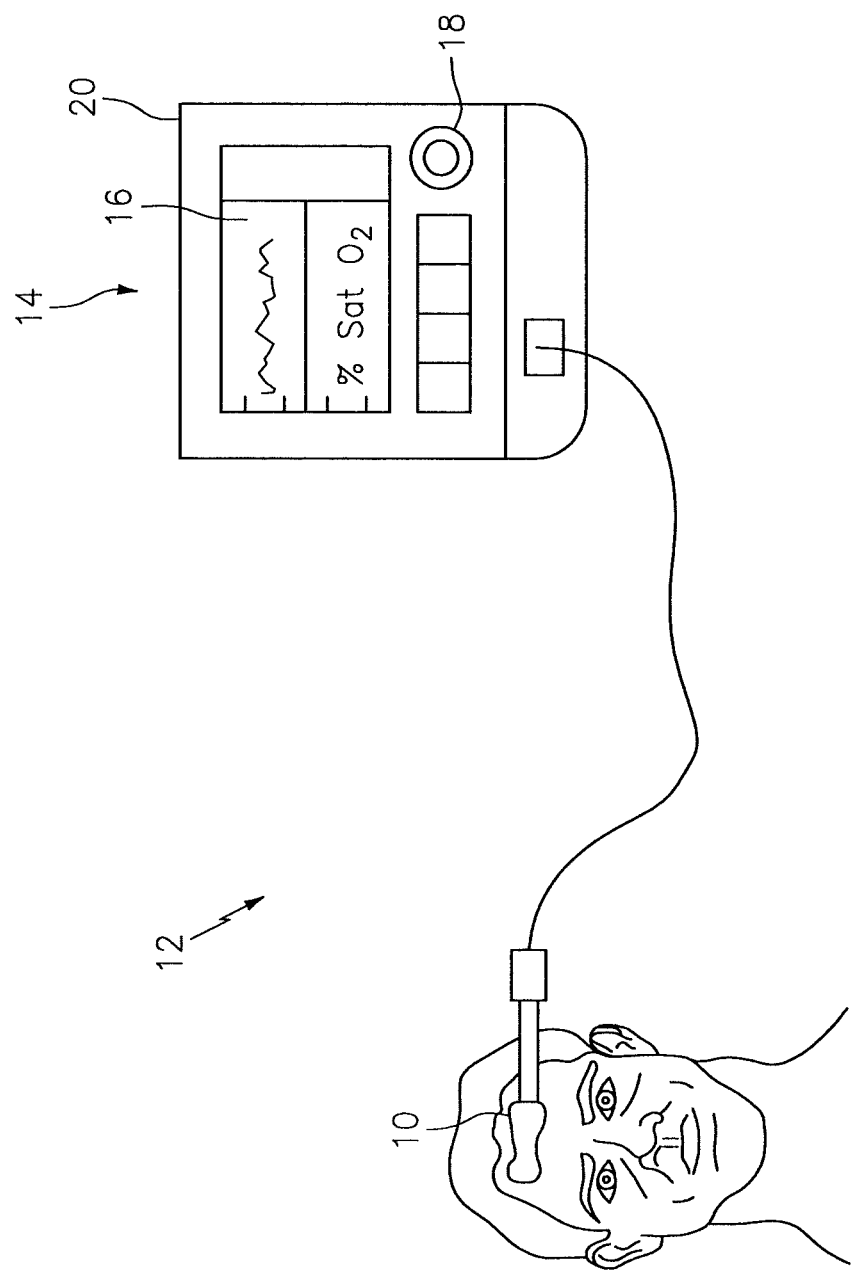
FIG. 1 is a diagrammatic view of a NIRS sensor assembly used in connection with a NIRS system.

The present disclosure describes embodiments of a NIRS sensor assembly; however, aspects of the present invention may be applied to other types of non-invasive medical devices, including, for example, pulse oximetry sensor assemblies.

The NIRS sensor assembly described herein can be used in connection with various types of NIRS systems. In the embodiment illustrated in FIG. 1, the NIRS sensor assembly 10 is used in connection with a NIRS system 12 that includes a base unit 14. The base unit 14 includes a display 16, operator controls 18, and a processor 20 for providing signals to and/or receiving signals from the NIRS sensor assembly 10. The processor 20 includes one or more central processing units (CPUs) adapted (e.g., programmed) to selectively perform the functions necessary to perform the functions described herein. One or more of the CPUs may be a microprocessor, co-processors, a micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in a memory (which memory may include a non-transitory computer readable medium). Note that when the processor implements one or more of its functions, the memory storing the corresponding operational instructions may be embedded within, or external to, the circuitry comprising processor. For example, the processor 20 is adapted to control the NIRS sensor assembly 10 to emit light signals from the light source 22, to receive sensor signals from the light detectors 24, 26, and to determine a characteristic of the tissue (e.g. blood oxygen saturation value) using the sensor signals. The processor 20 is further adapted for use with a NIRS sensor assembly 10 calibrated in the manner described below. U.S. Pat. Nos. 7,072,701 and 8,396,526, both of which are hereby incorporated by reference in their entirety, describe examples of NIRS oximetry systems having processors adapted to determine blood oxygen saturation values. The methodologies described in these patents are examples of methodologies that can be adapted pursuant to aspects of the present invention as will be described below. The present invention has broader applicability that these specific methodologies, however, and is therefore not limited to the methodologies described in these patents. The functionality of processor 20 may be implemented using hardware, software, firmware, or a combination thereof. A person skilled in the art would be able to adapt (e.g., program) the processor 20 to perform the functionality described herein without undue experimentation.

Referring to FIGS. 2-7, the NIRS sensor assembly 10 includes one or more light sources 22, one or more light detectors 24, 26, a circuit 28, a connector 30, a pad 32, a subject contact layer 34, and a cover 36. In some embodiments, including the embodiment illustrated in FIGS. 2-7, the NIRS sensor assembly 10 may additionally include a cover 36. The NIRS sensor assembly 10, and/or features of the NIRS sensor assembly 10, may be described as having a length extending along an x-axis, a width extending along a y-axis, and/or a height extending along a z-axis. The drawings illustrate the respective axes.

The light source 22 includes one or more light emitting components (e.g., light emitting diodes ("LEDs"), laser diodes, etc.) that are selectively operable to emit light at one or more predetermined wavelengths through an active region. The light emitted by the light source 22 includes light in the infrared range (i.e., in the wavelength range of about seven hundred nanometers (700 nm) to about one thousand nanometers (1,000 nm)) and/or the visible range (i.e., in the wavelength range of about three hundred ninety nanometers (390 nm) to about seven hundred fifty nanometers (750 nm)). The light source 22 may be mounted on the circuit 28 for electrical connection to the base unit 14 (see FIG. 1), as will be described below.

The light detectors 24, 26 each include one or more light detecting components (e.g., photodiodes, charge-coupled devices, etc.) that are selectively operable to detect light signals emitted by the light source 22 through an active region and produce signals representative of such detected light, which signals may be sent to the processor 20. The light detectors 24, 26 may detect the light, for example, after it passes through a biological tissue (e.g. brain tissue) of a subject. The light detectors 24, 26 may be connected within the circuit 28 for electrical connection to the base unit 14

(see FIG. 1), as will be described below. As will also be described below, the NIRS sensor assembly 10 may be configured so that one or more of the light detectors 24, 26 can be used in measuring the optical transmissivity of the subject contact layer 34, and/or the optical transmissivity of one or more other components of the NIRS sensor assembly 10 that light signals are intended to pass through before being detected by the light detectors 24, 26.

The light source 22 and the light detectors 24, 26 can assume various relative positions on the NIRS sensor assembly 10. International Patent Application No. PCT/US12/24889, which is hereby incorporated by reference in its entirety, discloses several examples of acceptable relative positions. The relative position of the light source 22 and the light detectors 24, 26 may preferably be selected so that: (1) the light source 22 and the light detectors 24, 26 are at least substantially linearly aligned along a lengthwise-extending axis 38 (see FIG. 2); and (2) the separation distances between the light source 22 and each of the light detectors 24, 26 are not the same.

The circuit 28 electrically connects the light source 22 and the light detectors 24, 26 to the connector 30. The connector 30, in turn, provides the structure that allows the NIRS sensor assembly 10 to be electrically connected to the base unit 14 (see FIG. 1). The NIRS sensor assembly 10 can include various types of circuits 28. In the embodiments illustrated in FIGS. 1-7, the circuit 28 is a flexible circuit that is similar to ones described in U.S. Patent Application No. 61/735,318, which is hereby incorporated by reference in its entirety. The present sensor assembly 10 is not limited to using a flexible circuit.

Figure 2:
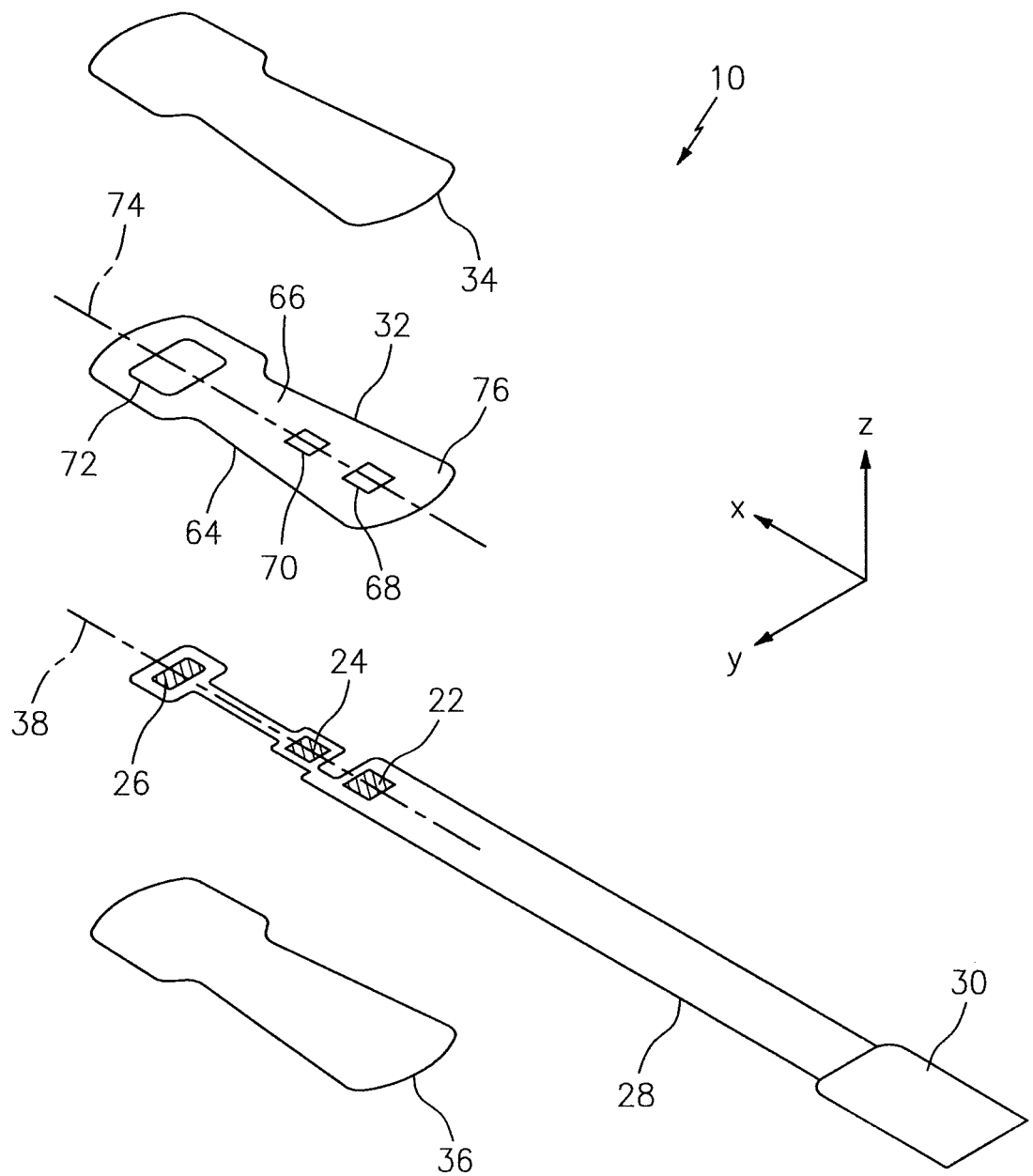
FIG. 2 is an exploded plan view of a NIRS sensor assembly of FIG. 1.
Figure 3:
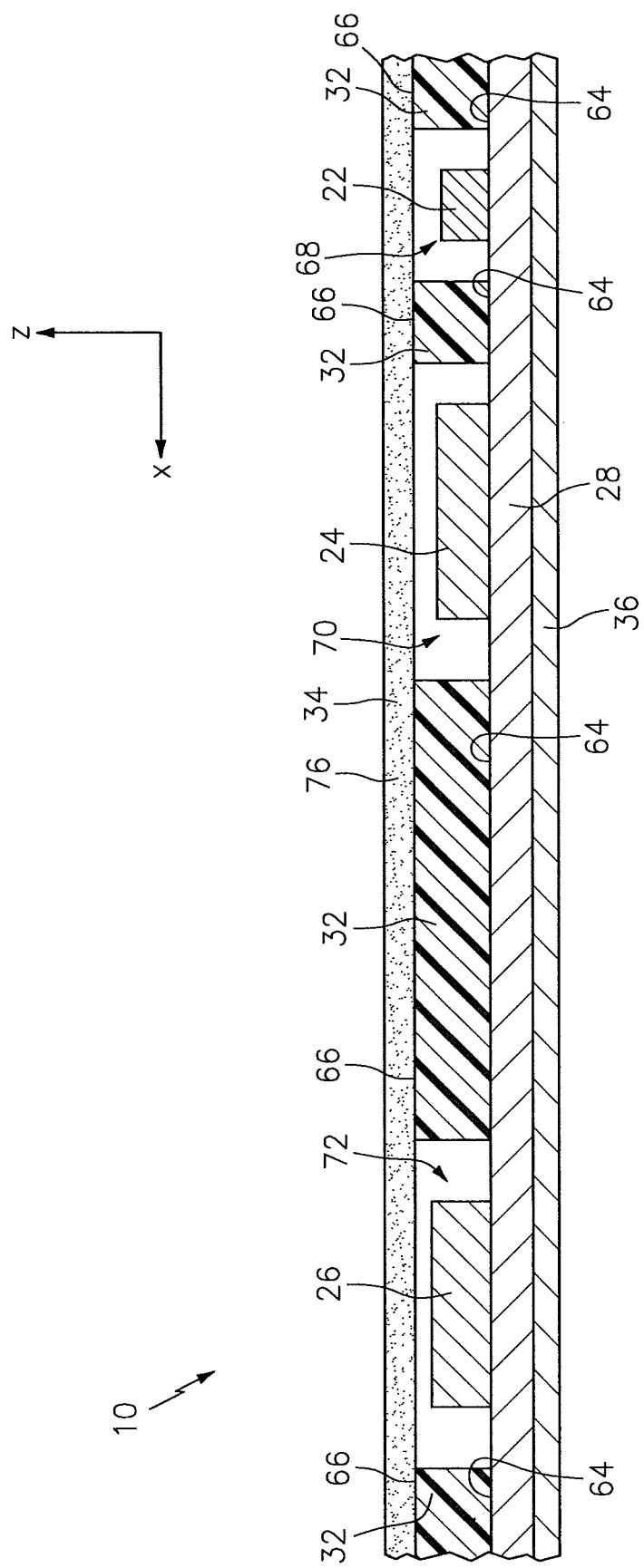
FIG. 3 is a sectional elevation view of the NIRS sensor assembly of FIG. 1.
Figure 4:
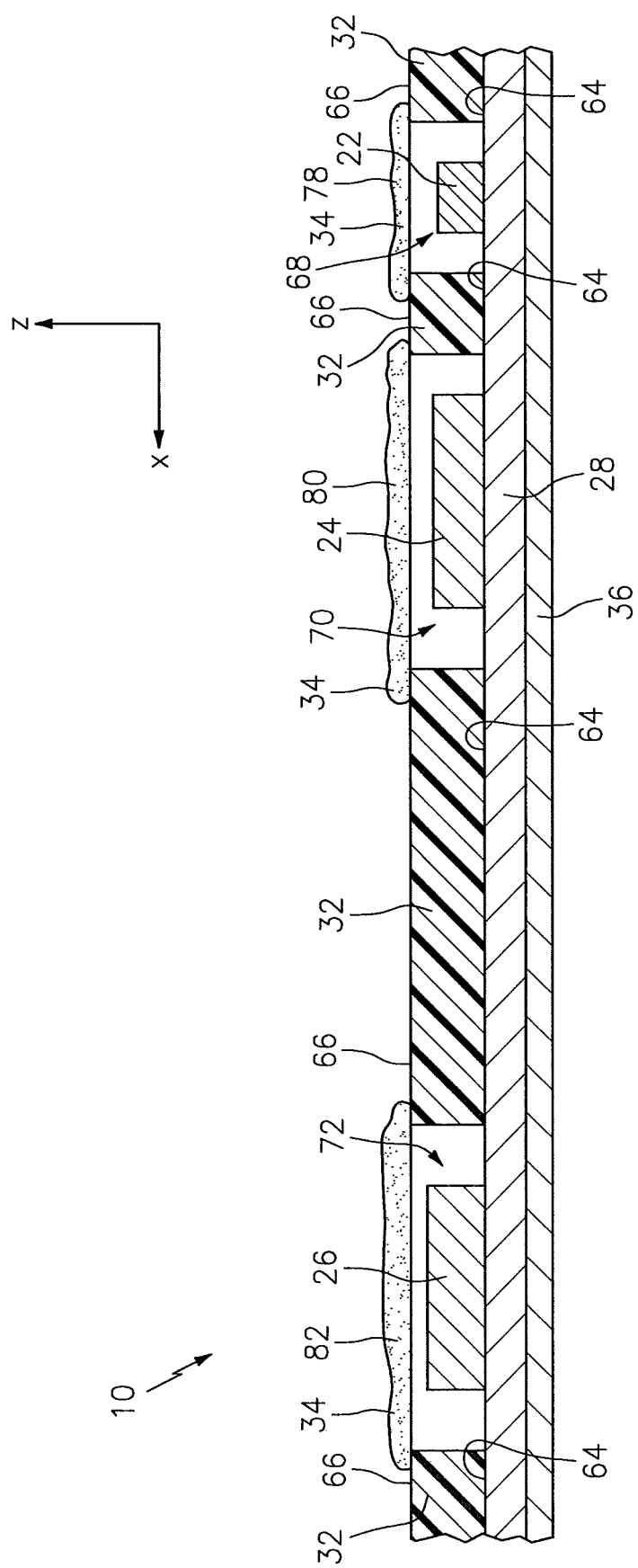
FIG. 4 is a sectional elevation view of another NIRS sensor assembly.
Figure 5:
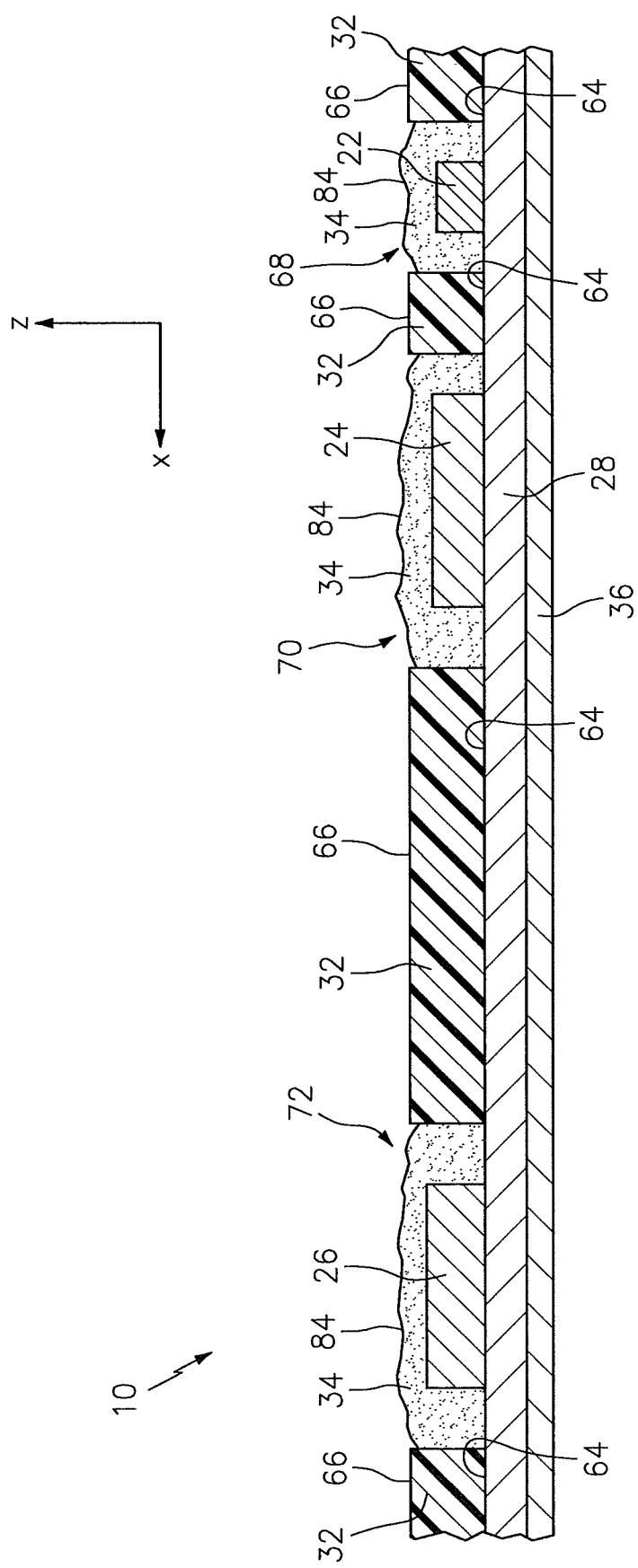
FIG. 5 is a sectional elevation view of another NIRS sensor assembly.
Figure 6:
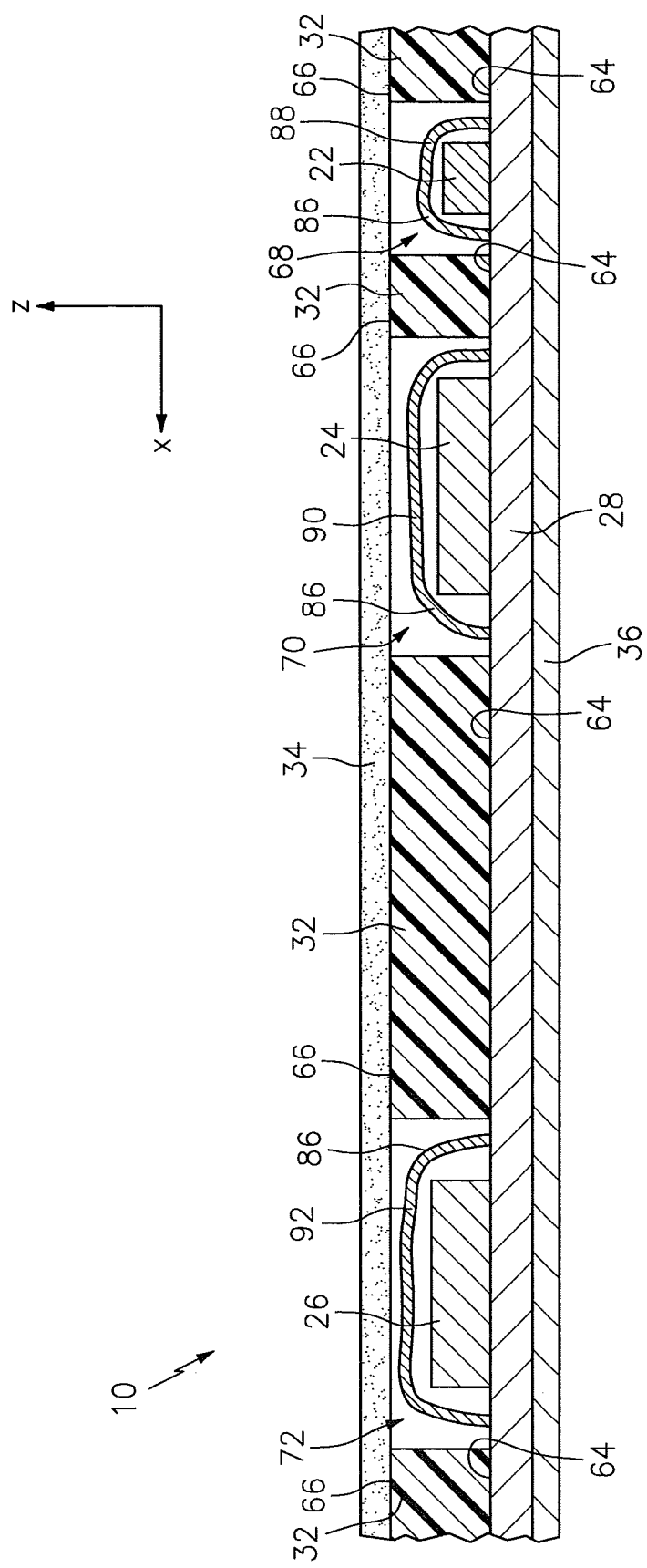
FIG. 6 is a sectional elevation view of another NIRS sensor assembly.
Figure 7:
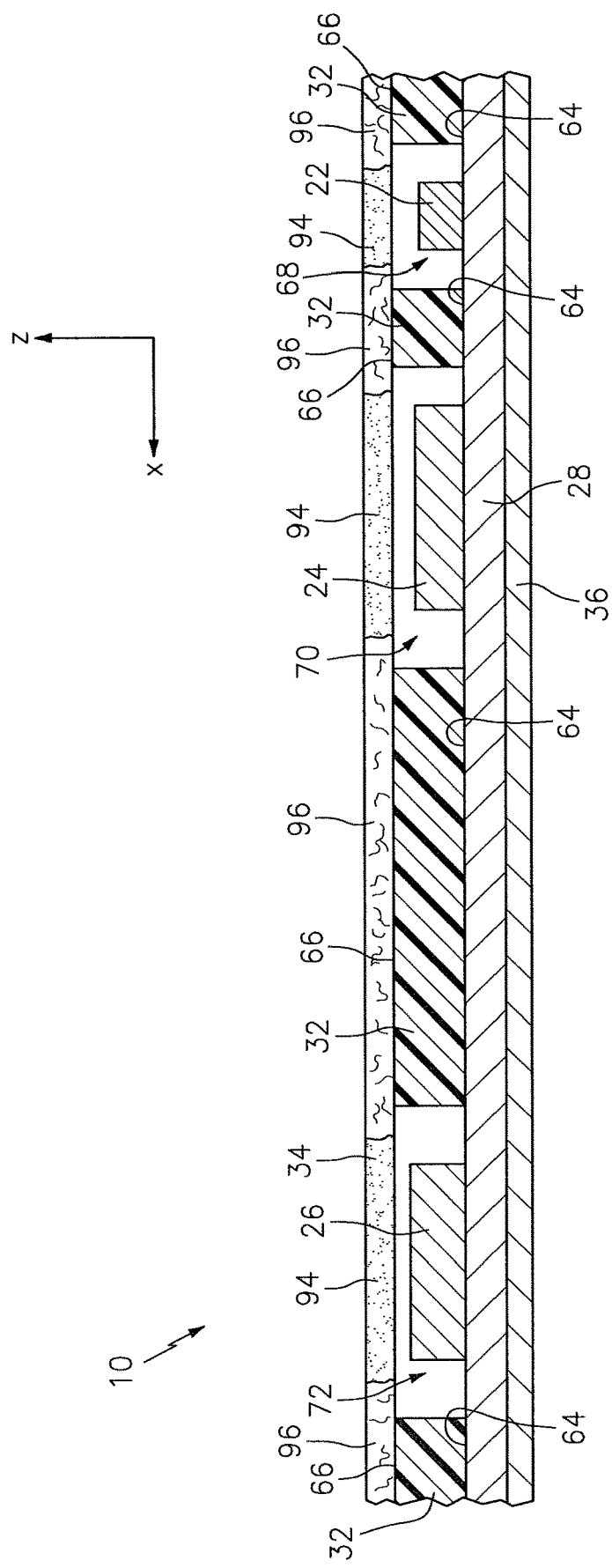
FIG. 7 is a sectional view of another NIRS sensor assembly.

Referring to FIGS. 1 and 2, the connector 30 is configured to provide electrical communication, directly or indirectly, between the NIRS sensor assembly 10 and the base unit 14. The NIRS sensor assembly 10 can include various types of connectors 30. In some embodiments, the connector 30 may be the same as or similar to the connectors disclosed in International Patent Application No. PCT/US12/24889, and in U.S. Provisional Patent Application No. 61/717,401, both of which are hereby incorporated by reference in their entirety. In some embodiments, the present NIRS sensor assembly 10 may not include a connector 30.

Referring to FIGS. 2-7, the pad 32 is disposed relative to the circuit 28. The pad 32 includes a bottom surface 64 and an opposing top surface 66, one or more side surfaces 67 that extend between the bottom surface 64 and the top surface 66, at least one light source aperture 68 that extends in a height wise direction between the bottom surface 64 and the top surface 66, and one or more light detector apertures 70, 72 that extend in a height wise direction between the bottom surface 64 and the top surface 66. The one or more side surfaces 67 collectively form the periphery of the pad 32. The pad 32 is not limited to this particular embodiment.

The pad 32 may be optically non-transmissive. The term "optically non-transmissive" is used herein relative to the pad 32 to describe that light signals emitted by the light source 22 during normal operation of the NIRS sensor assembly 10 may be blocked or otherwise prevented from passing through the pad 32 to an extent that any light signals that do pass through and exit the pad 32 have a luminescent intensity that is inadequate for a NIRS measurement.

The pad 32 may be positioned on the NIRS sensor assembly 10 so that the light source 22 is at least partially disposed within the light source aperture 68, and so that the light detectors 24, 26 are at least partially disposed within the respective light detector apertures 70, 72. The bottom surface 64 of the pad 32 may be attached (e.g., using an adhesive), directly or indirectly, to the circuit 28. In the embodiments illustrated in FIGS. 2-7, the bottom surface 64 of the pad 32 is attached directly to the circuit 28. The pad 32 can have various geometries. In the embodiment illustrated in FIG. 2, the geometry of the pad 32 is such that the light source aperture 68 and the light detector apertures 70, 72 are linearly aligned along a lengthwise-extending axis 74.

The pad 32 can be made from various materials or combinations of materials. An example of an acceptable material for the pad 32 is one that is soft and pliable, and suitable for a patient environment. A specific example of an acceptable pad 32 material is Poron® cellular urethane foam, a product of Rogers Corporation of Woodstock, Conn., U.S.A.

Now referring to FIGS. 10-15E, according to an aspect of the present disclosure a NIRS sensor assembly 10 may include a pad 32 (or other NIRS sensor assembly element) that includes one or more deflection elements 98. Each deflection element 98 is disposed within at least one surface 64, 66 of the pad 32, extends in a height wise direction (along the Z-axis) a distance between the bottom surface 64 and the top surface 66, and extends a distance within the body of the pad 32 (e.g. between the side surfaces 67). In some embodiments, a deflection element may break through one or more side surfaces, but preferably deflection elements do not break through a side surface 67, as will be explained below. In some embodiments, a deflection element 98 may be configured as a slot that extends between the bottom surface 64 and the opposing top surface 66; i.e. providing an open passage between the bottom surface 64 and the opposing top surface 66 (e.g. see FIG. 15A). In some embodiments, a deflection element 98 may be configured as a channel having a width 100 and a depth 102 (e.g. along the Z-axis; e.g. see FIGS. 15B-15E). The channel depth 102 extends from one of the bottom surface 64 or the top surface 66 toward the other of the top surface 66 or bottom surface 64. In the channel embodiments, the channel depth 102 is less than the distance between the top surface 66 and bottom surface 64 (i.e. the height wise thickness of the pad 32), and consequently the channel does not provide an open passage between the bottom surface 64 and the opposing top surface 66. The pad 32 may include channel type deflection elements 98 disposed in both the bottom surface 64 and the top surface 66, and in those instances the channel type deflection elements 98 may be offset from one another (e.g. see FIG. 15D) or they may be aligned with one another (e.g. see FIG. 15E). The present disclosure is not limited to deflection elements 98 configured to have a slot or a channel configuration. For example, a deflection element 98 may include a plurality of aligned smaller voids that collectively function as a slot, and similarly a deflection element 98 may include a plurality of aligned smaller voids that collectively function as a channel. In those embodiments that include a slot (unitary or collective), the slot may have a uniform width throughout the slot, or the width may vary at one or more points along the length of the slot. In those embodiments that include a channel (unitary or collective), the channel may have a uniform width and/or depth throughout the channel, or the width and/or depth may vary at one or more points along the length of the channel. The present disclosure is not limited to deflection elements 98 having any particular void geometry. In addition, a NIRS sensor assembly 10 according to the present disclosure may have one or more deflection elements 98 and is not limited to any particular number of deflection elements 98. Furthermore, a NIRS sensor assembly 10 according to the present disclosure having one or more deflection elements 98 may include a plurality of different configuration deflection elements 98; e.g. a NIRS sensor assembly 10 may both channels and slots, or a plurality of slots with a first slot having a first slot configuration and a second slot having a second slot configuration which second slot configuration is different from the first slot configuration, or a plurality of channels with a first channel having a first channel configuration and a second channel having a second channel configuration which second channel configuration is different from the first channel configuration, or combinations thereof, etc.

Figure 16A:
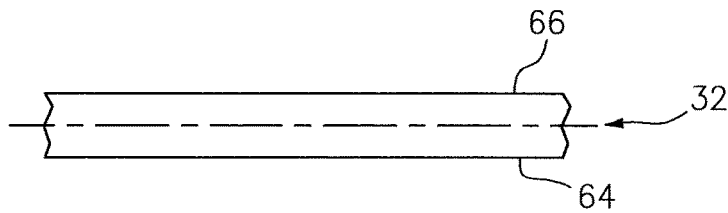
FIG. 16A is a diagrammatic side view of a pad section shown in a straight configuration.
Figure 16B:
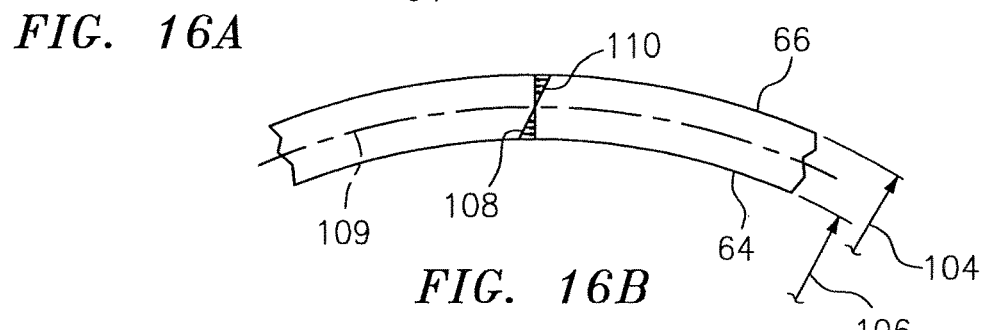
FIG. 16B is a diagrammatic side view of a pad section shown in a curved configuration.

In many applications, it is desirable to attach a NIRS sensor assembly 10 to a user skin surface that is curved. The term "curved" as used herein refers to a surface that is not a flat planar surface. A "curved' surface may have a constant radius, but more likely is one that has a complex curvature with different surface regions having different curvatures, and in particular may have one or more regions with a multi-dimensional curvature (e.g. two or three dimensional curvatures). As a result, the NIRS sensor assembly 10 is forced to bend (i.e. elastically deform) to conform to the curved surface. To facilitate the present description, portions of the bent NIRS sensor assembly 10 may be described as having a surface with an outer diameter 104 and a surface with an inner radius 106, where the diameter of the inner radius 106 is less than that of the outer radius 104. For example, as can be seen in FIG. 16B the pad 32 may be bent to conform to a curved surface, with the top surface 66 disposed at an outer radius 104 and the bottom surface disposed at an inner radius 106 that is less than the outer radius 104. As indicated above, a NIRS sensor assembly 10 may assume various different curvatures when conforming to a user's skin; e.g. in some applications the pad top surface 66 may assume the inner radius and the bottom surface 64 the outer radius that is greater than the inner radius, and different sections of the NIRS sensor assembly 10 may assume different curvatures.

A NIRS sensor assembly 10 according to the present disclosure can be customized with deflection elements 98 suited for different applications. For example, a NIRS sensor assembly 10 intended for use in an adult cerebral sensing application may be configured with a particular arrangement of one or more deflection elements 98 that are specifically chosen based on empirical data regarding an expected skin surface curvature; e.g. statistically significant empirical data may reveal that a high percentage of adult users have nearly the same skin surface curvature in the region where a cerebral sensor would be attached. The present NIRS sensor assembly 10 can be configured with a particular arrangement of one or more deflection elements 98 that are specifically chosen for that identified skin surface curvature. Alternatively, a NIRS sensor assembly 10 intended for use in a pediatric cerebral sensing application may be configured with a particular arrangement of one or more deflection elements 98 that are specifically chosen based on statistically significant empirical data regarding an expected skin surface curvature in pediatric patients. The present disclosure NIRS assembly therefore includes deflection element configurations customized for different applications.

When the pad 32 (or a portion thereof) is bent from a straight configuration (e.g. see FIG. 16A) to a curved configuration (i.e. not straight; e.g. see FIG. 16B), a portion 108 of the pad material (shown in FIG. 16B below the neutral axis 109 of the pad 32) will be in compression, and a portion 110 of the pad material (shown in FIG. 16B above the neutral axis of the pad 32) will be in tension. In this configuration, the elastic material of the pad 32 resists the bending and seeks to elastically return to the straight configuration. Furthermore, in those instances where the pad 32 comprises an open cell foam material some open cells may be compressed and desirable airflow through the pad 32 is inhibited.

The deflection elements 98 of the present disclosure address this issue and are preferably placed in regions of the pad where bending of the NIRS sensor assembly is anticipated. For example, in FIG. 12 the pad 32 is shown having a first deflection element 98a disposed between the near and far light detectors 24, 26 (near and far detector apertures 72, 70), a second deflection element 98b disposed between the near light detector 24 and the light source 22 (near detector aperture 70 and light source aperture 68), a third deflection element 98c disposed on a first lateral side of the light source 22, and a fourth deflection element 98d disposed on a second lateral side of the light source 22, opposite the first lateral side. In this particular NIRS sensor assembly 10 configuration, the deflection elements 98a-98d are advantageously positioned in regions where deflection of the NIRS sensor assembly 10 is typical when applied to a user's skin. The present disclosure is not limited to using any particular number of deflection elements 98, or any particular positioning of the deflection elements 98.

Figure 17A:
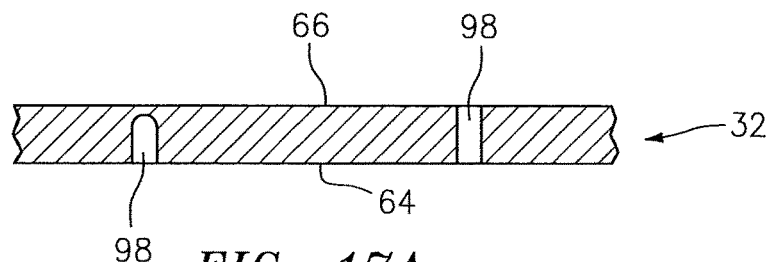
FIG. 17A is a diagrammatic sectional view of a pad section shown in a straight configuration, illustrating deflection element embodiments.
Figure 17B:
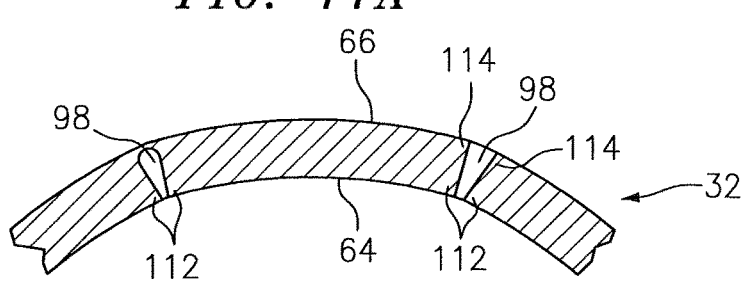
FIG. 17B is a diagrammatic sectional view of a pad section shown in a curved configuration, illustrating deflection element embodiments.

As can be seen in FIGS. 17A and 17B, when a NIRS sensor assembly according to the present disclosure is bent from a straight configuration (e.g. FIG. 17A) into a curved configuration (e.g. FIG. 17B) sections 112 of the pad 32 adjacent the deflection elements 98 deflect into the voids created by the deflection elements 98 and/or sections 114 of the pad 32 move away from one another (depending on the particular curvature assumed), thereby facilitating the bending of the pad 32 and consequently the application of the pad 32 to the user's skin. The deflection elements 98 thereby decrease the amount of compression and tension forces within the pad 32 that would otherwise resist the bending of the pad 32 and facilitate application of NIRS sensor assembly 10 to the user's skin.

In the preferred embodiments wherein the deflection elements 98 do not break through the respective side surface 67, the length (e.g., "X"; see FIG. 12) of pad material disposed between the end of the deflection element 98 and the respective side surface 67 (which length is substantially shorter than the length (e.g. "Y" see FIG. 12) of the deflection element 98) may still be subject to compression and tension forces as described above, but the amount of such forces is substantially less than there would be in the absence of the deflection element 98. Hence, the bending is facilitated. The pad material disposed between the end of the deflection element 98 and the respective side surface 67 (i.e. a slot or channel that does not break through to a side surface 67) prevents the entry of ambient light or fluids into the body of the pad 32 via the side surface 67. Alternatively, in some embodiments the deflection element 98 may break through the respective side surface 67, and a filler material can be inserted adjacent the side surface 67; e.g. a filler material that is operable to prevent the entry of ambient light or fluids into the body of the pad. The filler material is preferably one that possesses the same bending characteristics as the pad material, or one that can be more readily deformed (i.e. improved bending characteristics relative to the pad material) during bending.

The deflection elements 98 of the present disclosure are described above as being disposed in a pad 32 element of the NIRS sensor assembly 10. The deflection elements 98 may be disposed in other elements of the NIRS sensor assembly 10 alternatively, or in addition to deflection elements 98 disposed in the pad 32.

Referring to FIGS. 2-7, the subject contact layer 34 is disposed relative to the pad 32 to cover exposed portions of the light detectors 24, 26 and, in some embodiments, exposed portions of the light source 22. The subject contact layer 34 includes a bottom surface 33 and an opposing top surface 35. In some embodiments, the subject contact layer 34 may be in the faun of a sheet that is connected (e.g., using adhesives), either directly or indirectly, to the circuit 28. In the embodiments illustrated in FIGS. 2-6, for example, the subject contact layer 34 is in the form of a sheet, and the bottom surface 33 of the subject contact layer 34 is attached directly to the top surface 66 of the pad 32. In other embodiments, the subject contact layer 34 may be in the form of a coating that is disposed at least partially within one or more of the apertures 68, 70, 72 within the pad 32. In the embodiment illustrated in FIG. 7, for example, the subject contact layer 34 is in the form of a coating that is disposed within each of the light source aperture 68 and the light detector apertures 70, 72 of the pad 32.

One or more portions, or all portions, of the subject contact layer 34 are optically transmissive. In some embodiments, one or more portions of the subject contact layer 34 may be optically non-transmissive. The term "optically transmissive" is used herein relative to portions of the subject contact layer 34 to describe that light signals emitted by the light source 22 during normal operation of the NIRS sensor assembly 10 may pass through and exit the portions with a luminescent intensity that is adequate for a NIRS measurement. The term "optically non-transmissive" is used herein relative to portions of the subject contact layer 34 to describe that light signals emitted by the light source 22 during normal operation of the NIRS sensor assembly 10 are blocked or otherwise prevented from passing through the portions to an extent that any light signals that do pass through and exit the portions have a luminescent intensity that is inadequate for a NIRS measurement. The terms "optically transmissive" and "optically non-transmissive" are not used herein to describe visual transparency to the human eye, or visual non-transparency to the human eye. The term "optical transparency" is used herein relative to the subject contact layer 34 to describe that light at wavelengths and intensity transmitted by the light source and collected by the light detectors, can transmit through the subject contact layer 34 and into the subject tissue, or can transmit through the subject contact layer 34 from the subject tissue, and be detected by the light detectors. The optical transmissivity of the subject contact layer 34 may depend on one or more characteristics of the subject contact layer 34, including, for example, a dimension of the subject contact layer 34, and/or a material of the subject contact layer 34. In some embodiments, for example, the optical transmissivity may depend on a distance that extends in a height wise direction between the bottom surface 33 and the top surface 35 of the subject contact layer 34.

The subject contact layer 34 is positioned on the NIRS sensor assembly 10 so that the one or more portions of the subject contact layer 34 that are optically transmissive are aligned with the active region of the light source 22 and the active regions of each of the light detectors 24, 26. In the embodiment illustrated in FIG. 4, for example, the subject contact layer 34 includes optically transmissive portions 94 aligned with active regions of the light source 22 and the light detectors 24, 26, and optically non-transmissive portions 96 elsewhere. The subject contact layer 34 is positioned on the NIRS sensor assembly 10 so that the top surface 33 of the subject contact layer 34 may contact the subject tissue being sensed during operation of the NIRS sensor assembly 10. In some embodiments, the subject contact layer has a predetermined thickness and has known and/or uniform optical attenuation and scattering characteristics.

The subject contact layer 34 may include one continuous section, or a plurality of discrete sections. In the embodiments illustrated in FIGS. 2-4 and 6, the subject contact layer 34 includes one continuous section. In the embodiment illustrated in FIGS. 5 and 7, however, the subject contact layer 34 includes three discrete sections 37, 39, 41. The subject contact layer 34 can have various geometries. The geometry of the subject contact layer 34 may be such that the subject contact layer 34 is operable to cover the entire top surface 66 of the pad 32, or the geometry may be such that the subject contact layer 34 is operable to cover only one or more portions of the top surface 66 of the pad 32. In the embodiment shown in FIGS. 3, 4, and 6, for example, the subject contact layer 34 is attached to and covers the entire top surface 66 of the pad 32, including the light source aperture 68 and the light detector apertures 70, 72. In the embodiment shown in FIG. 5, in contrast, the three discrete sections 37, 39, 41 of the subject contact layer 34 each cover a portion of the top surface 66 of the pad 32, leaving other portions of the top surface 66 exposed. In the embodiment shown in FIG. 5, the three discrete sections 37, 39, 41 of the subject contact layer 34 cover the light source aperture 68, the first light detector aperture 70, and the second light detector aperture 72, respectively.

The subject contact layer 34 can be made from various materials or combinations of materials. The subject contact layer 34 may include one or more foam materials, one or more woven fabric materials, one or more non-woven fabric materials, one or more gel materials, or a combination thereof. Examples of acceptable foam materials include: silicone foams; polyethylene foams; polyurethane foams; and polyvinyl chloride (PVC) foams. Examples of acceptable woven fabric materials include: tricot fabrics; knit fabrics; and loose weave fabrics. Examples of acceptable non-woven fabric materials include: spunlace fabrics; microporous fabrics; and elastic fabrics. Examples of acceptable gel materials include: hydrogel adhesives; hydrocolloid adhesives; encapsulated gels. In those embodiments that include an optically transparent portion 94 and an optically non-transparent portion 96, the material(s) of those portions 94, 96 may be different from one another. A specific example of an acceptable optically transparent material is a polyethylene foam product with a pressure sensitive adhesive offered by Avery Dennison, Inc., product name Avery-Med 362.

The subject contact layer 34 aids in reducing or eliminating discomfort to the subject that components of the NIRS sensor assembly 10 might otherwise cause the subject. For example, in certain applications it is possible that the light source 22 may act as a heat source that, over time, can cause the subject to experience discomfort in the absence of the subject contact layer 34. In such applications, the subject contact layer 34 may act as a thermal barrier that decreases the amount of thermal energy reaching the subject's skin from the light source. As another example, in certain applications it is possible that components in the NIRS sensor assembly 10 (e.g., the light source 22, the light detectors 26, 28, etc.) may create pressure points that can cause the subject discomfort in the absence of the subject contact layer 34. In such applications, the subject contact layer 34 may act as a cushioning layer that decreases the magnitude of, or eliminates, such pressure points. The cushioning effect produced by the subject contact layer 34 may be particularly advantageous in those applications where the subject's skin is fragile (e.g., neonatal skin, elderly skin, etc.).

In some embodiments, one or more components of the NIRS sensor assembly 10 may be disposed between the light source 22 and the subject contact layer 34, or between the light detectors 24, 26 and the subject contact layer 34. Those components include EMI shielding 86 that may be in the form of a single section, or a plurality of discrete sections. In the embodiment shown in FIG. 6, for example, the layer of EMI shielding 86 includes three discrete sections: a first section 88 disposed relative to the light source 22, a second section 90 disposed relative to the light detector 24 that is closest to the light source 22, and a third section 92 disposed relative to the light detector 26 that is farthest from the light source 22. The EMI shielding 86 may be made of any acceptable material, or combination of materials, operable to shield against EMI. Examples of acceptable EMI shielding 86 materials are disclosed in U.S. patent application Ser. No. 14/102,004. In some embodiments, one or more layers of electrically insulating material (not shown) may additionally or alternatively be disposed between the light source 22 and the subject contact layer 34, or between the light detectors 24, 26 and the subject contact layer 34. The layer of electrically insulating material may be made of any acceptable material, or combination of materials, that is electrically non-conductive. Examples of acceptable electrically insulating materials are disclosed in U.S. patent application Ser. No. 14/102,004. In some embodiments, one or more layers of EMI shielding 86 and/or one or more layers of electrically insulating material may be incorporated into the subject contact layer 34. For example, the subject contact layer 34 may include a plurality of sublayers, and a layer of EMI shielding 86 may be disposed between the sublayers.

Referring to FIGS. 2-7, the cover 36 is disposed relative to the circuit 28. In the embodiments illustrated in FIGS. 2-7, the cover 36 is attached (e.g., using adhesives) to the surface of the circuit 28 that is opposite the light source 22 and the light detectors 24, 26. The cover 36 can have various geometries. In FIG. 2, the cover 36 has a geometry that generally matches the geometry of the pad 32. The cover 36 can be made from various materials or combinations of materials. The cover 36 may preferably consist of a soft pliable material that can be used in a patient environment. Examples of acceptable cover 36 materials include: Tyvek®, a product made by DuPont; Poron® cellular urethane foam; vinyl materials, plastic materials; and foam materials.

Figure 8:
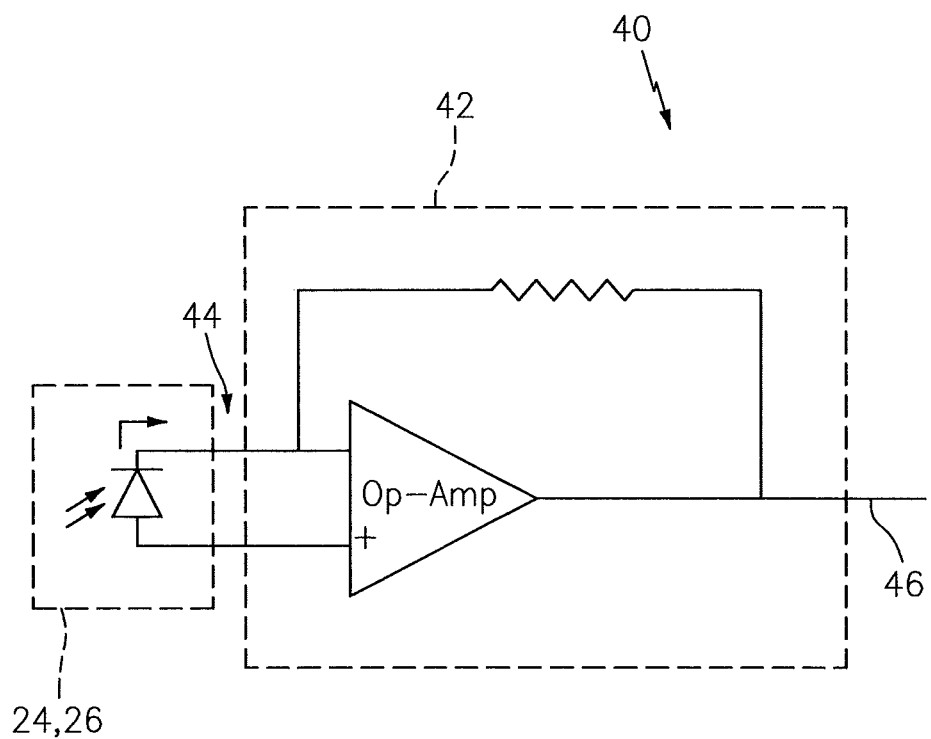
FIG. 8 is a circuit diagram showing a luminance measuring device.
Figure 9:
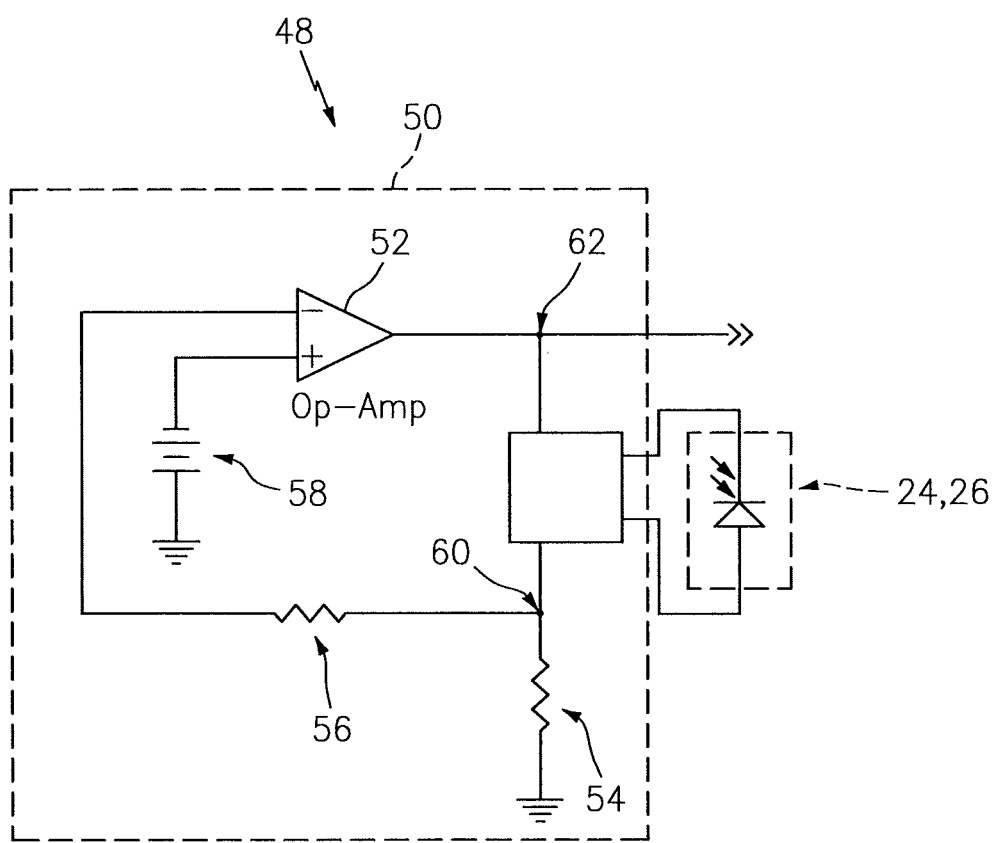
FIG. 9 is a circuit diagram showing a temperature measuring device.
Figure 10:
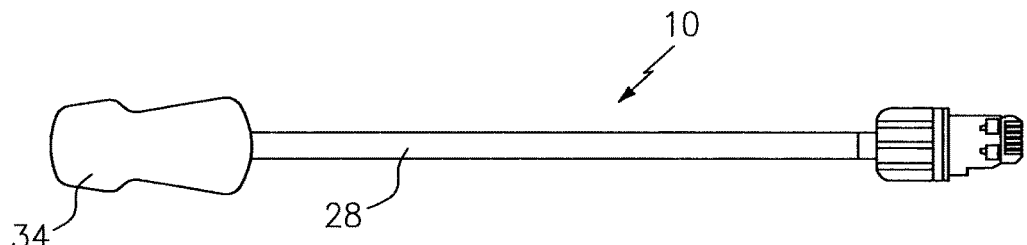
FIG. 10 is a diagrammatic planar view of an embodiment of the present NIRS sensor assembly.
Figure 11:
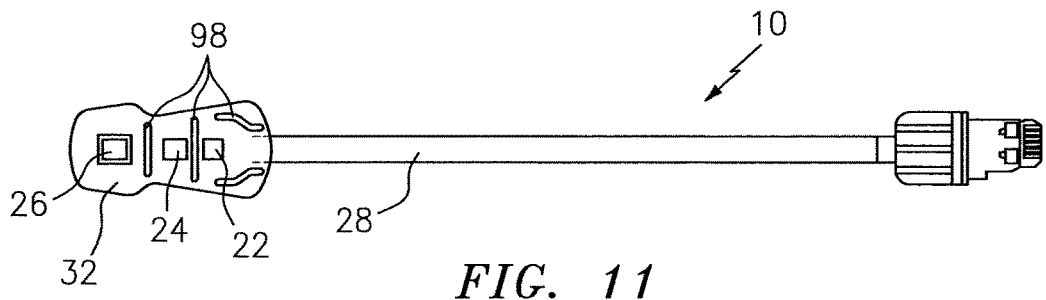
FIG. 11 is a diagrammatic planar view of an embodiment of the present NIRS sensor assembly, with a layer removed to show the pad.
Figure 12:
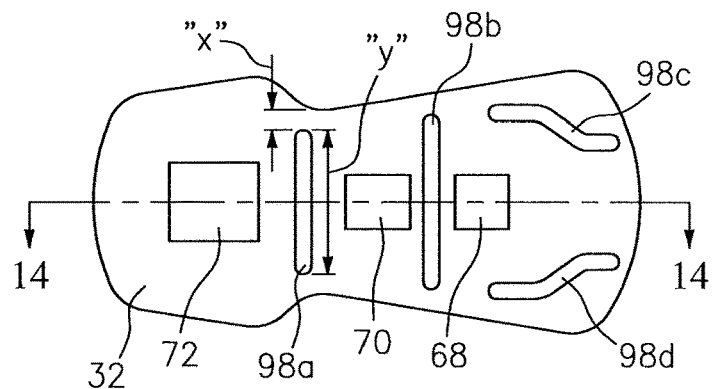
FIG. 12 is a diagrammatic planar top view of a pad embodiment.
Figure 13:
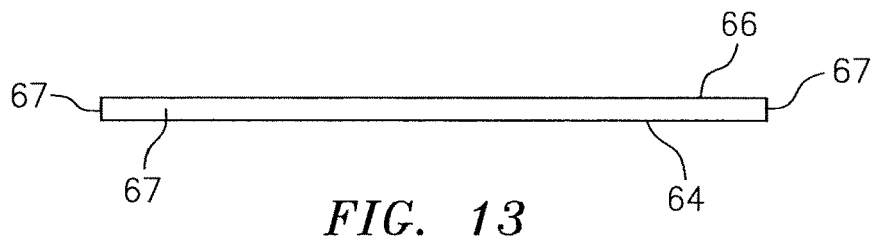
FIG. 13 is a diagrammatic side view of the pad embodiment shown in FIG. 12.
Figure 14:
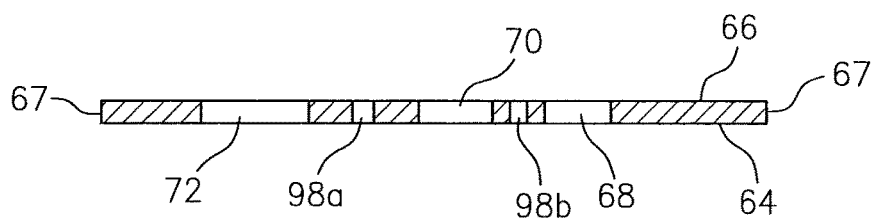
FIG. 14 is a diagrammatic sectional view of the pad embodiment shown in FIG. 12, taken at the section line 14-14.
Figures 15A, 15B, 15C:
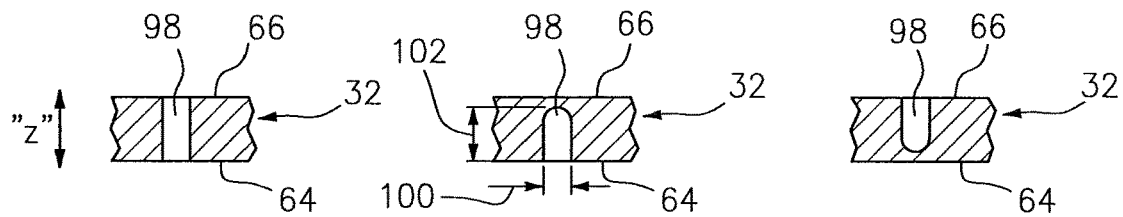
FIG. 15A is a diagrammatic sectional view of a pad embodiment illustrating a deflection element embodiment.
FIG. 15B is a diagrammatic sectional view of a pad embodiment illustrating a deflection element embodiment.
FIG. 15C is a diagrammatic sectional view of a pad embodiment illustrating a deflection element embodiment.
Figures 15D, 15E:
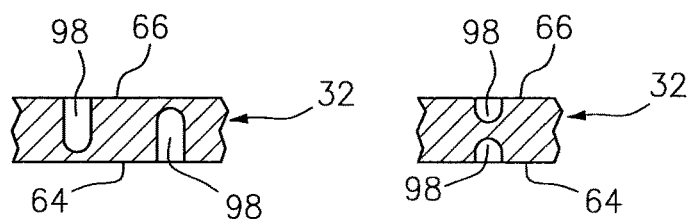
FIG. 15D is a diagrammatic sectional view of a pad embodiment illustrating a deflection element embodiment.
FIG. 15E is a diagrammatic sectional view of a pad embodiment illustrating a deflection element embodiment.

The NIRS sensor assembly 10 may be configured so that one or more of the light detectors 24, 26 can be used in measuring the luminance and/or temperature of the light source 22. For example, in some embodiments, one or more of the light detectors 24, 26 may be positioned sufficiently close to the light source 22 so that the luminance of light signals detected by one or more of the light detectors 24, 26 is indicative of the luminance of the light emitted by the light source 22, and so that the temperature of one or more of the light detectors 24, 26 is indicative of the temperature of the light source 22. The NIRS sensor assembly 10 may include a luminance measuring device that is operable to measure the luminance of light detected by one or more of the light detectors 24, 26. Examples of acceptable luminance measuring devices are disclosed in U.S. patent application Ser. No. 13/543,180, which is hereby incorporated by reference in its entirety. FIG. 8 illustrates an example of a luminance measuring device 40 that is operable to measure the luminance of light detected by one of the light detectors 24, 26. The luminance measuring device 40 includes a photovoltaic circuit 42 that is zero biased and has a zero ohm input impedance. The input 44 of the photovoltaic circuit 42 receives signals from one of the light detectors 24, 26. The output 46 of the photovoltaic circuit 42 provides luminance signals relating to the luminance of the respective light detector 24, 26, which luminance signals may be transmitted to the base unit 14 (see FIG. 1) for processing. The processor 20 of the base unit 14 (see FIG. 1) may adjust a characteristic (e.g., luminance) of the light emitted by the light source 22 in response to the luminance signals. The NIRS sensor assembly 10 may include a temperature measuring device that is operable to measure the temperature of one or more of the light detectors 24, 26. Examples of acceptable temperature measuring devices are disclosed in U.S. patent application Ser. No. 13/543,180. FIG. 9 illustrates an example of a temperature measuring device 48 that is operable to measure the temperature of one of the light detectors 24, 26. The temperature measuring device 48 includes a circuit 50 for converting a signal received from one of the light detectors 24, 26 into a temperature signal indicative of the temperature of the respective light detector 24, 26. The temperature measuring device 48 includes a circuit 50 that biases one of the light detectors 24, 26 with a constant current. The circuit 50 includes an op-amp 52, a first load 54, a second load 56 and a voltage source 58. The input 60 of the circuit 50 receives a signal from one of the light detectors 24, 26. The output 62 of the circuit 50 provides temperature signals relating to the temperature of the respective light detector 24, 26, which signals may be transmitted to the base unit 14 (see FIG. 1) for processing. The processor 20 of the base unit 14 (see FIG. 1) may adjust a characteristic (e.g., luminance) of the light signals emitted by the light source 22 in response to the temperature signals.

During operation of the NIRS sensor assembly 10, the NIRS sensor assembly 10 is positioned relative to a biological tissue of a subject. Light signals emitted by the light source 22 pass through the subject contact layer 34, enter and exit the subject's tissue, pass back through the subject contact layer 34, and are thereafter detected by the light detectors 24, 26. Signals representative of the light signals detected by the light detectors 24, 26 are relayed back to the base unit 14, where they are processed by the processor 20 to obtain data relating to one or more characteristics (e.g., blood oxygenation) of the subject's biological tissue.

According to an aspect of the present invention, the processor 20 is adapted for use with a sensor assembly having a contact layer 34 as is described above; e.g., the processor 20 is adapted for use with sensor assemblies that include a subject contact layer 34, including one or more algorithms that include calibration accounting for light signals passing through the subject contact layer 34.

According to an aspect of the present invention, the processor 20 may be adapted for use with a "contact layer sensor assembly" using empirically collected data. For example, the blood oxygen saturation level of a clinically appropriate number of subjects may be sensed using a contact layer sensor assembly (as described herein), while at the same time (or a point close in time) empirical oxygen saturation data can be collected from the same subjects by discrete sampling or continuous monitoring. The temporal and physical proximity of the NIRS sensing and the development of the empirical data helps assure accuracy. Calibration parameters that may be necessary to create agreement between the empirically determined data values and the oximeter sensed data values may be determined using techniques similar to those described in U.S. Pat. No. 7,072,701, and the processor 20 adapted accordingly. In this way, the optical characteristics of the "contact layer sensor assembly" will be accounted for in the calibration parameters.

Alternatively, the processor 20 may be calibrated for use with a contact layer sensor assembly by sensing a phantom sample having known optical characteristics, preferably similar to that of biological tissue that would ordinarily be sensed by the NIRS system; e.g., skin, bone, brain, etc.) In this embodiment, the phantom sample may be sensed with one or more sensor assemblies without a contact layer 34, and one or more sensor assemblies with a contact layer 34. The difference in light signal attenuation could then be used to calibrate the processor 20 for subsequent use with a contact layer sensor assembly as is described herein.

While several embodiments have been disclosed, it will be apparent to those of ordinary skill in the art that aspects of the present invention include many more embodiments. Accordingly, aspects of the present invention are not to be restricted except in light of the attached claims and their equivalents.

What is claimed is:

1. A near-infrared spectroscopy (NIRS) sensor assembly for measuring a characteristic of a biological tissue, the NIRS sensor assembly comprising:
   a light source operable to emit light at one or more predetermined wavelengths;
   at least one light detector having an active area for detecting light emitted by the light source and passed through the biological tissue, and which detector is operable to produce signals representative of the detected light; and
   a pad having a top surface, a bottom surface, and at least one side surface extending between the top and bottom surfaces, at least one light source aperture extending from the top surface to the bottom surface, at least one light detector aperture extending from the top surface to the bottom surface, and at least one deflection element configured as a void disposed in the pad, the void having a length extending between a first lengthwise end and an opposite second lengthwise end, and the deflection element being open to at least one of the top or bottom surfaces, a first light blocking portion of the pad disposed between the first lengthwise end of the at least one deflection element and the at least one side surface, and a second light blocking portion of the pad disposed between the second lengthwise end of the at least one deflection element and the at least one side surface.

2. The sensor assembly of claim 1, wherein the at least one deflection element is independent of the at least one light source aperture and the at least one light detector aperture.

3. The sensor assembly of claim 2, wherein the at least one deflection element extends from the bottom surface to the top surface, thereby providing an open passage between the bottom surface and the top surface.

4. The sensor assembly of claim 3, wherein the at least one deflection element is configured as a slot.

5. A near-infrared spectroscopy (NIRS) sensor assembly for measuring a characteristic of a biological tissue, the NIRS sensor assembly comprising:
   a light source operable to emit light at one or more predetermined wavelengths;
   at least one light detector having an active area for detecting light emitted by the light source and passed through the biological tissue, and which detector is operable to produce signals representative of the detected light; and
   a pad having a top surface, a bottom surface, and at least one side surface extending between the top and bottom surfaces, at least one light source aperture extending from the top surface to the bottom surface, at least one light detector aperture extending from the top surface to the bottom surface, and at least one deflection element comprising a plurality of voids linearly aligned with one another, each of the voids extending into the pad from a first surface opening in the top surface, or extending into the pad from a second surface opening in the bottom surface, or extending between the first surface opening in the top surface and the second surface opening in the bottom surface, and one or more light blocking portions of the pad disposed between each of the voids, and enclosing a periphery of each respective first surface opening in the top surface and second surface opening in the bottom surface.

6. The sensor assembly of claim 2, wherein the pad has a thickness, and the at least one deflection element has a width and a depth, which depth distance extends from the bottom surface or the top surface where the deflection element is open and extends toward the other of the top surface or bottom surface, and which depth distance is less than the thickness of the pad.

7. The sensor assembly of 6, wherein the depth is uniform along the length of the deflection element.

8. The sensor assembly of claim 6, wherein the deflection element is configured as a channel.

9. The sensor assembly of 2, wherein the deflection element has a uniform width along the length of the deflection element.

10. The sensor assembly of claim 2, wherein the at least one light detector includes a near light detector spaced a first distance from the light source and a far light detector spaced a second distance from the light source, which second distance is greater than the first distance; and
    wherein the at least one deflection element includes a first deflection element disposed between the near light detector and the far light detector, a second deflection element disposed between the near light detector and the light source, a third deflection element disposed on a first lateral side of the light source, and a fourth deflection element disposed on a second lateral side of the light source, opposite the first lateral side.

11. The sensor assembly of claim 1, wherein the at least one deflection element is open to the at least one of the top surface or bottom surface at an opening, and the opening has a periphery that is surrounded by a light-blocking pad material.

12. A near-infrared spectroscopy (NIRS) sensor assembly for measuring a characteristic of a biological tissue, the NIRS sensor assembly comprising:
    a light source operable to emit light at one or more predetermined wavelengths;
    at least one light detector having an active area for detecting light emitted by the light source and passed through the biological tissue, and which detector is operable to produce signals representative of the detected light; and
    a pad comprising a material, the pad having a top surface, a bottom surface, and at least one side surface extending between the top surface and the bottom surface, at least one light source aperture extending from the top surface to the bottom surface, at least one light detector aperture extending from the top surface to the bottom surface, and at least one deflection element configured as a void disposed in the pad, the deflection element extending into the pad from a first surface opening in the top surface, or extending into the pad from a second surface opening in the bottom surface, or extending between the first surface opening in the top surface and the second surface opening in the bottom surface, wherein said pad material encloses a periphery of the respective first surface opening in the top surface and second surface opening in the bottom surface.

13. The sensor assembly of claim 12, wherein the pad material enclosing the periphery of the respective first surface opening and the second surface opening is a pliable foam that is optically non-transmissive.

* * * * *